United States Patent [19]

Mais et al.

[11] Patent Number: 5,210,343
[45] Date of Patent: May 11, 1993

[54] PROCESS FOR THE PREPARATION OF P-DICHLOROBENZENE

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 854,121

[22] Filed: Mar. 19, 1992

[30] Foreign Application Priority Data

Mar. 27, 1991 [DE] Fed. Rep. of Germany ........ 4110051

[51] Int. Cl.$^5$ ........................ C07C 17/12; C07C 25/08
[52] U.S. Cl. .................................... 570/210; 570/207; 570/208; 570/209
[58] Field of Search ................ 570/208, 210, 207, 209

[56] References Cited

U.S. PATENT DOCUMENTS

| 4,647,709 | 3/1987 | Wolfram | 570/210 |
| 4,851,596 | 7/1989 | Mais et al. | 570/210 |
| 4,990,707 | 2/1991 | Mais et al. | 570/210 |

FOREIGN PATENT DOCUMENTS

| 0126669 | 11/1984 | European Pat. Off. | 570/209 |
| 0474074 | 3/1992 | European Pat. Off. | 570/209 |

OTHER PUBLICATIONS

Patent Abstracts of Japan, vol. 9, No. 278, Nov. 1985 & JP-A-60 125 251 (Ihara Chemical Kogyo KK).
Patent Abstracts of Japan, vol. 9, No. 293, Nov. 1985 & JP-A-60 136 576 (Ihara Chemical Kogyo KK).

*Primary Examiner*—Werren B. Lone
*Attorney, Agent, or Firm*—Spung Horn Kramer & Woods

[57] ABSTRACT

Dichlorobenzene having an increased p-content and a greatly reduced m-content is obtained by ring chlorination of benzene or chlorobenzene in the presence of Friedel-Crafts catalysts if the reaction is carried out in the presence of co-catalysts of the formula (I)

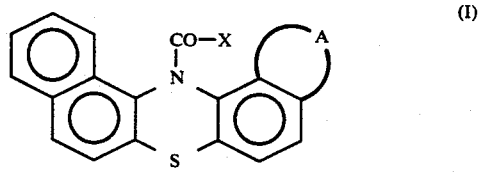

wherein
X represents fluorine, chlorine, bromine, trifluoromethyl or pentafluoroethyl and
A represents 2 hydrogen atoms or the group —CH=CH—CH=CH—.

10 Claims, No Drawings

PROCESS FOR THE PREPARATION OF P-DICHLOROBENZENE

The present invention relates to the preparation of p-dichlorobenzene by ring chlorination of benzene or chlorobenzene in the presence of Friedel-Crafts catalysts and in the presence of co-catalysts in the liquid phase.

p-Dichlorobenzene is a useful intermediate product for the synthesis of, for example, dyestuff and drug precursors. It is furthermore used as an important monomer for the preparation of the high-quality plastic polyphenylene sulphide. A high purity of the p-dichlorobenzene is important especially for its use as a drug precursor and as a raw material for polyphenylene sulphide. In particular, it should contain the isomeric dichlorobenzenes, o-dichlorobenzene and m-dichlorobenzene, in only very small amounts.

Ring chlorination of benzene initially gives chlorobenzene, which can be further chlorinated to give a mixture of the three isomeric dichlorobenzenes. Chlorobenzene can therefore also be used as the starting substance for the preparation of dichlorobenzene.

The chlorination is in general carried out in the liquid phase using gaseous chlorine and in the presence of Friedel-Crafts catalysts, such as, for example, iron(III) chloride. A dichlorobenzene fraction which consists of about 59% of o-dichlorobenzene, about 39% of p-dichlorobenzene and about 2% of m-dichlorobenzene is thus obtained with FeCl$_3$ as the catalyst at a chlorination temperature of 70° C. (Ullmanns Encyklopädie der technischen Chemie (Ullmann's Encyclopaedia of Industrial Chemistry), 4th edition 1975, Volume 9, page 504). Because of the very similar boiling points of the m- and p-dichlorobenzene, separation of the isomers by distillation results only in a separation into o-dichlorobenzene and a mixture of m- and p-dichlorobenzene. Another purification or separation step, such as, for example, separation on zeolites or melt crystallisation, must be carried out to remove the m-dichlorobenzene.

By co-catalysts in addition to the Friedel-Crafts catalyst, the isomer composition of the dichlorobenzene mixture can be changed so that a higher proportion of p-dichlorobenzene is formed. Examples of such co-catalysts are sulphur or disulphur dichloride (Ullmann's Encyclopedia of Industrial Chemistry, 5th edition, Volume A6, page 336) and phenothiazines which carry substituents on the N atom (EP-A-126,669).

However, the co-catalysts are not able to suppress the formation of the m-isomer completely. An m-/p-dichlorobenzene fraction having an m-content of 0.5 to 1.0% is thus obtained using sulphur as the co-catalyst. An m-/p-dichlorobenzene fraction having an m-content of 0.36% is obtained using N-chlorocarbonylphenothiazine as the co-catalyst (Example 3, EP-A-126,669) at a chlorination temperature of 60° C. It is therefore necessary for these mixtures also to be further processed to highly pure p-dichlorobenzene by the abovementioned methods.

The chlorination of benzene or chlorobenzene in the presence of certain zeolites is furthermore known (EP-A-118,851, EP-A-195,514, EP-A-225,723, EP-A-231,133, EP-A-273,736 and US-A-4,777,305); other substances having a co-catalytic action can also be added in this variant in the presence of zeolites (EP-A-154,236, EP-A-231,662, DE-A-3,720,391 and EP-A-248,931). Disadvantages of catalysis by zeolites are in general the high requirement of 2 to 6% by weight of zeolite, based on the substrate, and furthermore the fact that in general the chlorination waste gas obtained in this process still contains significant amounts of chlorine escaping in unused form, as well as HCl. In general, detectable amounts of m-dichlorobenzene, about 1.0 to 2.0% in the m-/p-dichlorobenzene fraction, are also formed here.

A process has now been found for the preparation of dichlorobenzene having an increased p-content and a very greatly reduced m-content by ring chlorination of benzene or chlorobenzene in the presence of Friedel-Crafts catalysts and in the presence of co-catalysts in the liquid phase, which is characterised in that one or more substances of the formula (I)

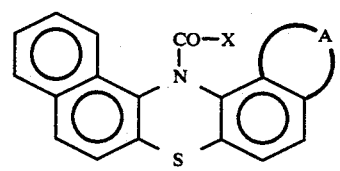

in which
X represents fluorine, chlorine, bromine, trifluoromethyl or pentafluoroethyl and
A represents 2 hydrogen atoms or the group —CH=CH—CH=CH—
are employed as the co-catalyst.

The co-catalysts which can be employed according to the invention can be prepared by methods which are known in principle, for example by sulphurisation of the corresponding diarylamines with sulphur to give the 1,4-thiazine derivative and subsequent derivatisation on the nitrogen (Kehrmann et al., Chem. Ber. 55, 2346 (1922)).

The process according to the invention is carried out in the liquid phase, it also being possible for the substrate benzene or chlorobenzene, or a mixture of these, to be diluted with a solvent which is inert towards chlorine, such as, for example, methylene chloride, chloroform, carbon tetrachloride, perchloroethylene or the like. The reaction is preferably carried out without a solvent. Chlorine is passed into the reaction mixture in gaseous form as the chlorinating agent.

The reaction pressure is in principle not critical; it can be normal, reduced or elevated. The reaction is preferably carried out under normal pressure.

A possible reaction temperature for the ring chlorination according to the invention is in principle the range between the solidification point and the boiling point of the reaction mixture. The reaction temperature is preferably 10° to 80° C., particularly preferably 40° to 70° C.

The water content of the reaction mixture is in general not critical. It is therefore preferred not to dry all the starting substances specifically, but to employ them with the low water content with which they are usually present in the chemical industry. However, it is also possible for all or some of the starting substances to be dried. In general, the water content of the starting substances should not be above the saturation limits at the reaction temperature chosen. The water contents in the reaction mixture are preferably not more than 250 ppm, particularly preferably not more than 100 ppm.

Friedel-Crafts catalysts which can be employed are the customary Lewis acids known for this purpose to the expert, or elements which form Lewis acids under the reaction conditions (Ullmann's Encyclopedia of Industrial Chemistry, 5th edition, Volume A6, page 343). These are, for example, the elements iron, antimony, aluminium, gallium and others which are known to the expert, or chalcogenides or halides thereof, such as, for example, iron(III) chloride, antimony(III) chloride, aluminium chloride, antimony oxychloride, iron sulphide and others. Iron or iron(III) chloride or a mixture of these is preferably employed.

The amounts of Friedel-Crafts catalyst to be employed according to the invention are in the range from 0.001 to 1% by weight, preferably in the range from 0.01 to 0.1% by weight, based on the benzene or chlorobenzene or mixture thereof.

The amounts of co-catalysts to be employed according to the invention are in the range from 0.001 to 2% by weight, preferably in the range from 0.01 to 0.5% by weight, based on benzene or chlorobenzene or the mixture thereof. The amount of co-catalyst employed is to be chosen here so that the molar ratio of Friedel-Crafts catalyst and co-catalyst is in a range from 10:1 to 1:10. The molar ratio preferably employed is 2:1 to 1:2, particularly preferably about 1:1.

The process according to the invention gives a particularly high content of p-dichlorobenzene coupled with a greatly reduced content of m-dichlorobenzene in the dichlorination of benzene or the chlorination of chlorobenzene or the chlorination of a mixture of the two. The more greatly pronounced p-directing effect compared with the prior art is decidedly surprising, since it is expressly emphasised in EP-A-126,669 (page 2, lines 11 to 17) that additional substitution on the benzene rings of the phenothiazine system has no further substantial influence on the co-catalysis. However, the co-catalysts according to the invention result in p-selectivities which are significantly increased further.

The marked reduction, according to the invention, of the m-content in the chlorination mixture or in the dichlorobenzene fraction likewise goes far beyond the prior art. According to the invention, it is possible to push the m-content in the chlorination mixture below the gas chromatography detection limit of about 0.03% by weight. Together with the high p-contents, this means that an m-/p-mixture having a p-content of greater than 99.9% can be obtained directly by distillation. Subsequent further purification or separation of isomers can therefore be omitted for most purposes.

The following examples illustrate the invention, but without limiting it to these.

EXAMPLE 1

100 parts by weight of benzene were initially introduced into a reactor and. 0.051 part by weight of FeCl₃ and 0.123 part by weight of the co-catalyst of the formula

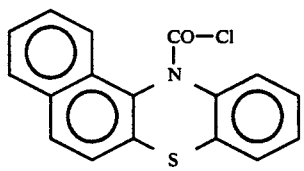

were added. The mixture was then heated to 60° C., while stirring, and 127.5 parts by weight of gaseous chlorine were uniformly passed in at this temperature in the course of 4.5 hours. The product mixture was analysed by area-calibrated gas chromatography. The composition was as follows:

| benzene | 0.16% |
|---|---|
| chlorobenzene | 42.95% |
| o-dichlorobenzene | 8.22% |
| m-dichlorobenzene | n.d. |
| p-dichlorobenzene | 48.67% |
| trichlorobenzenes | n.d. |

(n.d. denotes content less than 0.03%)

The ratio of p-dichlorobenzene to o-dichlorobenzene was thus p/o=5.92 and the ratio of p-dichlorobenzene to m-dichlorobenzene was p/m≧1662.3.

A corresponding result was obtained by employing as the co-catalyst 0.143 part by weight of the co-catalyst of the formula

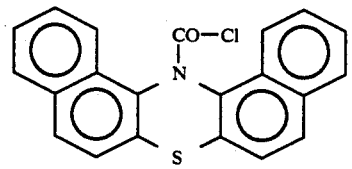

EXAMPLE 2

100 parts by weight of chlorobenzene were introduced into a reactor, 0.222 part by weight of FeCl₃ and 0.57 part by weight of the co-catalyst of the formula

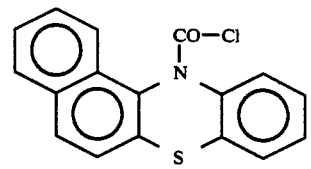

were added and the temperature was thermostatically controlled at 20° C. 0.53 part by weight of gaseous chlorine was uniformly passed in at this temperature in the course of 4.0 hours. The composition of the chlorination mixture was as follows:

| benzene | 12.90% |
|---|---|
| o-dichlorobenzene | 9.46% |
| m-dichlorobenzene | n.d. |
| p-dichlorobenzene | 77.64% |
| trichlorobenzenes | n.d. |

(n.d. denotes content less than 0.03%)

The p/o ratio is thus p/o=8.20 and the p/m ratio is p/m≧2588.0.

EXAMPLE 3

The process of Example 1 was repeated, except that instead of the co-catalyst in that example, 0.107 part by weight of the co-catalyst of the formula

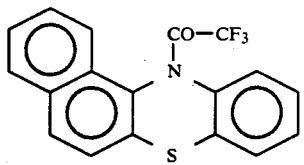

was employed. The composition of the chlorination mixture was as follows:

| | |
|---|---|
| benzene | 0.08% |
| chlorobenzene | 42.78% |
| o-dichlorobenzene | 9.88% |
| m-dichlorobenzene | 0.05% |
| p-dichlorobenzene | 47.21% |
| trichlorobenzenes | n.d. |

(n.d. denotes content less than 0.03%)

The p/o ratio was thus p/o=4.78 and the p/m ratio was p/m=944.2.

COMPARISON EXAMPLE 4 (according to EP-A-126,669)

0.050 part by weight of FeCl₃ and 0.103 part by weight of N-chlorocarbonylphenothiazine were dissolved in 100 parts by weight of benzene and the solution was heated to 60° C., while stirring. 136.7 parts by weight of gaseous chlorine were then uniformly passed in over a period of 4.5 hours. The composition of the chlorination mixture was as follows:

| | |
|---|---|
| benzene | 0.33% |
| chlorobenzene | 43.40% |
| o-dichlorobenzene | 9.79% |
| m-dichlorobenzene | 0.15% |
| p-dichlorobenzene | 46.28% |
| trichlorobenzenes | 0.05% |

The p/o ratio was thus p/o=4.73 and the p/m ratio was p/m=308.5.

Comparison Example 4 shows significantly lower p/o and p/m ratios, especially in comparison with Example 1. At the same time, it can be seen by comparison of the two amounts of chlorine passed in (127.5 parts by weight in Example 1 and 136.7 parts by weight in Comparison Example 4) that the chlorination according to the invention proceeds with a considerably better chlorine yield, since the two mixtures show approximately the same conversion.

We claim:

1. A process for the preparation of dichlorobenzene having an increased p-content and a very greatly reduced m-content by ring chlorination of benzene or chlorobenzene with chlorine in the presence of a catalytic amount of a Friedel-Crafts catalyst and a co-catalyst in the liquid phase, wherein the co-catalyst has the following formula

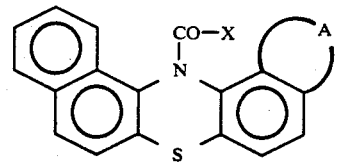

in which
X represents fluorine, chlorine, bromine, trifluoromethyl or pentafluoroethyl and
A represents 2 hydrogen atoms or the group —CH=CH—CH=CH—
and wherein the reaction is carried out at a temperature between the solidification point and the boiling point of the reaction mixture.

2. Process according to claim 1, characterised in that a substance of the following formula

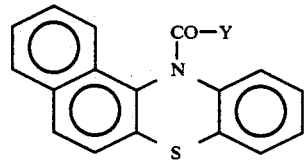

in which
Y represents chlorine or trifluoromethyl is employed as the co-catalyst.

3. Process according to claim 1, characterised in that iron or iron(III) chloride is employed as the Friedel-Crafts catalyst.

4. Process according to claim 1, characterised in that Friedel-Crafts catalyst is employed in an amount of 0.001 to 2% by weight based on the amount of benzene or chlorobenzene.

5. Process according to claim 1, characterised in that the co-catalyst is employed in an amount of 0.001 to 5% by weight based on the amount of benzene or chlorobenzene.

6. Process according to claim 1, characterised in that the molar ratio of Friedel-Crafts catalyst to co-catalyst is chosen as 10:1 to 1:10.

7. The process of claim 1, in which the Friedel-Crafts catalyst is employed in an amount of 0.01 to 0.2% by weight based on the amount of benzene or chlorobenzene.

8. The process of claim 1, in which the co-catalyst is employed in an amount of 0.01 to 0.5% by weight based on the amount of benzene or chlorobenzene.

9. The process of claim 1, in which the molar ratio of Friedel-Crafts catalyst to co-catalyst is chosen as 2:1 to 1:2.

10. The process of claim 1, in which the reaction is carried out at a temperature of 10° to 80° C.

* * * * *